(12) United States Patent
Nishikawa et al.

(10) Patent No.: US 9,974,862 B2
(45) Date of Patent: May 22, 2018

(54) LIPID PARTICLES AND NUCLEIC ACID DELIVERY CARRIER

(71) Applicant: FUJIFILM Corporation, Tokyo (JP)

(72) Inventors: Naoyuki Nishikawa, Ashigarakami-gun (JP); Makoto Ono, Ashigarakami-gun (JP); Susumu Sugiyama, Ashigarakami-gun (JP); Yoshihide Iwaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 15/406,232

(22) Filed: Jan. 13, 2017

(65) Prior Publication Data

US 2017/0119887 A1 May 4, 2017

Related U.S. Application Data

(63) Continuation of application No. PCT/JP2015/070397, filed on Jul. 16, 2015.

(30) Foreign Application Priority Data

Jul. 17, 2014 (JP) ................................ 2014-146808

(51) Int. Cl.
| | | |
|---|---|---|
| *A61K 47/22* | (2006.01) | |
| *A61K 47/24* | (2006.01) | |
| *A61K 47/28* | (2006.01) | |
| *A61K 47/34* | (2017.01) | |
| *A61K 9/16* | (2006.01) | |
| *C12N 15/113* | (2010.01) | |

(52) U.S. Cl.
CPC ............ *A61K 47/34* (2013.01); *A61K 9/1617* (2013.01); *A61K 9/1641* (2013.01); *A61K 47/22* (2013.01); *A61K 47/24* (2013.01); *A61K 47/28* (2013.01); *C12N 15/113* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,851,510 A | 12/1998 | Counsell et al. | |
| 8,236,943 B2 * | 8/2012 | Lee .................... | A61K 9/0019 435/450 |
| 2003/0069392 A1 * | 4/2003 | Lin .................... | C07D 233/64 530/330 |
| 2007/0135370 A1 * | 6/2007 | MacLachlan ...... | C12N 15/1131 514/44 A |
| 2011/0293695 A1 | 12/2011 | Panzner et al. | |
| 2013/0171241 A1 | 7/2013 | Geall | |
| 2014/0227345 A1 | 8/2014 | Essler et al. | |

FOREIGN PATENT DOCUMENTS

| | | |
|---|---|---|
| JP | 10-504021 A | 4/1998 |
| JP | 2005-517739 A | 6/2005 |
| JP | 2011-021026 A | 2/2011 |
| WO | 97/049723 A1 | 12/1997 |
| WO | 2012/000104 A1 | 1/2012 |

OTHER PUBLICATIONS

Extended European Search Report dated Jun. 14, 2017, issued from the Europe Patent Office in corresponding European Patent Application No. 15821518.6.
Lasic, D.D., *Recent developments in medical applications of liposomes: sterically stabilized liposomes in cancer therapy and gene delivery in vivo*, Journal of Controlled Release, vol. 48, 1997, pp. 203-222, (20 pages total).
Okano, T. (ed.), Introduction to Modern Pharmaceutics (revised third edition), Nankodo Co., Ltd., Apr. 10, 1987, pp. 285-286 (4 pages).
International Preliminary Report on Patentability issued from the International Bureau in counterpart International Application No. PCT/JP2015/070397, dated Jan. 26, 2017.
Office Action dated Jul. 11, 2017, from the Japanese Patent Office in counterpart Japanese Application No. 2014-146808.
International Search Report for PCT/JP2015/070397 dated Oct. 6, 2015 [PCT/ISA/210].
JJ Wheeler et al., Stabilized Plasmid-Lipid Particles: Construction and Characterization, Gene Therapy, vol. 6, pp. 271-281, 1999.
Hongtao LV et al.; Toxicity of Cationic Lipids and Cationic Polymers in Gene Delivery, Journal of Controlled Release, vol. 114, pp. 100-109, 2006.

(Continued)

*Primary Examiner* — Richard A Schnizer
(74) *Attorney, Agent, or Firm* — Sughrue Mion, PLLC

(57) ABSTRACT

An object of the present invention is to provide lipid particles which have low cytotoxicity, can stably hold nucleic acid molecules outside cells, and can promptly release nucleic acids in cytoplasm after escaping from endosome, and a nucleic acid delivery carrier. According to the present invention, there are provided lipid particles containing a compound represented by the following General Formula (1), sterol, at least one lipid selected from the group consisting of a neutral lipid and a lipid having a polyethylene glycol chain, and nucleic acids, and a nucleic acid delivery carrier.

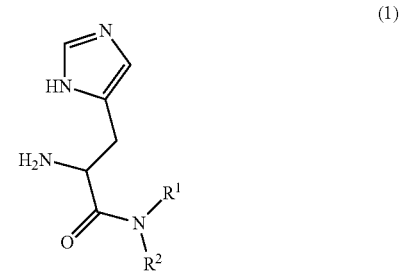

(1)

In the formula, $R^1$ and $R^2$ are the same as or different from each other, and are alkyl groups having 10 to 22 carbon atoms.

8 Claims, 3 Drawing Sheets

(56) References Cited

OTHER PUBLICATIONS

Written Opinion for PCT/JP2015/070397 dated Oct. 6, 2015 [PCT/ISA/237].
Teisuke Okano; Introduction to Modern Pharmeceutics (Revised $3^{rd}$ Edition); Nankodo Co., Ltd.; pp. 285-286; Apr. 10, 1987.

* cited by examiner

SEQUENCE LISTING

<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 1
guucagacca cuucagcuu                                          19

<210> SEQ ID NO 2
<211> LENGTH: 19
<212> TYPE: RNA

```
<213> ORGANISM: Artificial Sequence
<220> FEATURE:
<223> OTHER INFORMATION: Synthetic siRNA

<400> SEQUENCE: 2
caagucuggu gaagucgaa                                              19
```

LIPID PARTICLES AND NUCLEIC ACID DELIVERY CARRIER

CROSS-REFERENCE TO RELATED APPLICATIONS

The present application is a continuation of PCT/JP2015/070397 filed on Jul. 16, 2015 and claims priority under 35 U.S.C. § 119 of Japanese Patent Application No. 146808/2014 filed on Jul. 17, 2014.

BACKGROUND OF THE INVENTION

1. Field of the Invention

The present invention relates to lipid particles and an application thereof, and suitably relates to lipid particles which is useful for delivering nucleic acids into cells, and a nucleic acid delivery carrier.

2. Description of the Related Art

Nucleic acid medicines are disclosed as next-generation pharmaceutical products since an action mechanism thereof with respect to a disease is obvious and there are few adverse reactions. For example, nucleic acid medicines in which RNA interference (RNAi) is used can cause decomposition of mRNA of a target gene existing in a cell and can inhibit expression of the target gene. As a result, it is possible to reduce or treat diseases and symptoms caused by abnormal expression of a specific gene or a gene group. Nucleic acids, for example, siRNA, are used in such nucleic acid medicines in which RNA interference is used. However, it is necessary to deliver nucleic acids into cells in order to exhibit a function with these nucleic acids.

In general, a carrier (vector) is used in methods for effectively delivering nucleic acids into cells. Examples of the carrier (vector) include a viral carrier and a non-viral carrier. Since viral carrier has highly unclear points in terms of pathogenicity, immunogenicity, and safety in cytotoxicity, it is desired to use an non-viral carrier from the viewpoint of the safety.

A cationic carrier which can hold nucleic acids through an electrostatic interaction is used as the non-viral carrier since nucleic acids are anionic. A cationic liposome in which cationic lipids having a specific structure are used or a composite in which a cationic polymer is used is generally known as an example of the cationic carrier.

As an example of the cationic liposome, a liposome formed of cationic lipids, 1,2-dioleoyl-3-sn-phosphatidylethanolamine (DOPE), and polyethylene glycol lipids is disclosed in Gene Therapy, Vol. 6, p. 271, 1999. In addition, lipid particles formed of a first cationic lipid, a second cationic lipid, a neutral lipid, and a polyethylene glycol lipid are disclosed in WO2012-00104A in addition to lipid particles containing 50 mol % to 85 mol % cationic lipids.

Furthermore, a composite in which a cationic polymer is used is also known (Journal of Controlled Release 114 (2006) pp. 100 to 109).

In addition, as examples of means for further improving the cationic carrier in which cationic lipids are used, an amphoteric liposome in which cationic lipids and anionic lipids are combined is disclosed in JP2011-21026A, and an amphoteric liposome formed of amphoteric amphiphilic lipids is disclosed in JP2005-517739A.

SUMMARY OF THE INVENTION

However, there are many carriers, in which cationic lipids are used and which have strong cytotoxicity, and similarly, there is also a problem of cytotoxicity in a composite in which a cationic polymer is used. Therefore, the carriers are not satisfactory. An amphoteric liposome has been reviewed as means for solving the problem of the cationic carriers. However, the amphoteric liposome is not ready for practical use and it cannot be said that the amphoteric liposome is sufficient as means for solving the problem.

An object of the present invention is to provide lipid particles which have low cytotoxicity, can stably hold nucleic acid molecules outside cells, and can promptly release nucleic acids in cytoplasm after escaping from endosome, and a nucleic acid delivery carrier in which the lipid particles are used.

The present inventors have conducted extensive studies in order to solve the above-described problem. As a result, they have found that it is possible to provide lipid particles by which the above-described problem is solved using lipid particles containing a compound represented by the following General Formula (1) (where $R^1$ and $R^2$ are the same as or different from each other and are alkyl groups having 10 to 22 carbon atoms), sterol, at least one lipid selected from the group consisting of a neutral lipid and a lipid having a polyethylene glycol chain, and nucleic acids, and have completed the present invention.

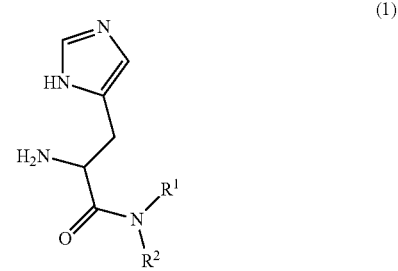

That is, means for solving the problem is as follows.

[1] Lipid particles comprising: a compound represented by the following General Formula (1); sterol; at least one lipid selected from the group consisting of a neutral lipid and a lipid having a polyethylene glycol chain; and nucleic acids,

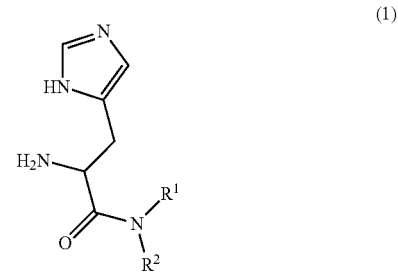

in the formula, $R^1$ and $R^2$ are the same as or different from each other, and are alkyl groups having 10 to 22 carbon atoms.

[2] The lipid particles according to [1], in which the content of the compound represented by General Formula (1) is 15 mol % to 60 mol %.

[3] The lipid particles according to [1] or [2], in which the content of sterol is 10 mol % to 50 mol %.

[4] The lipid particles according to any one of [1] to [3], in which the content of at least one lipid selected from the group consisting of a neutral lipid and a lipid having a polyethylene glycol chain is 3 mol % to 55 mol %.

[5] The lipid particles according to any one of [1] to [4], in which the sterol is cholesterol.

[6] The lipid particles according to any one of [1] to [5], in which the neutral lipid is phosphatidylcholine.

[7] The lipid particles according to any one of [1] to [6], in which the lipid having a polyethylene glycol chain is phosphoethanolamine which has been modified with polyethylene glycol.

[8] A nucleic acid delivery carrier comprising: a compound represented by the following General Formula (1); sterol; at least one lipid selected from the group consisting of a neutral lipid and a lipid having a polyethylene glycol chain; and nucleic acids,

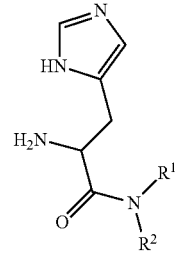

(1)

in the formula, $R^1$ and $R^2$ are the same as or different from each other and are alkyl groups having 10 to 22 carbon atoms.

The lipid particles of the present invention have low cytotoxicity. In addition, according to the lipid particles of the present invention, nucleic acids are efficiently released in a target cell, and therefore, it is possible to obtain significantly favorable drug efficacy.

DESCRIPTION OF THE PREFERRED EMBODIMENTS

Figure 1:
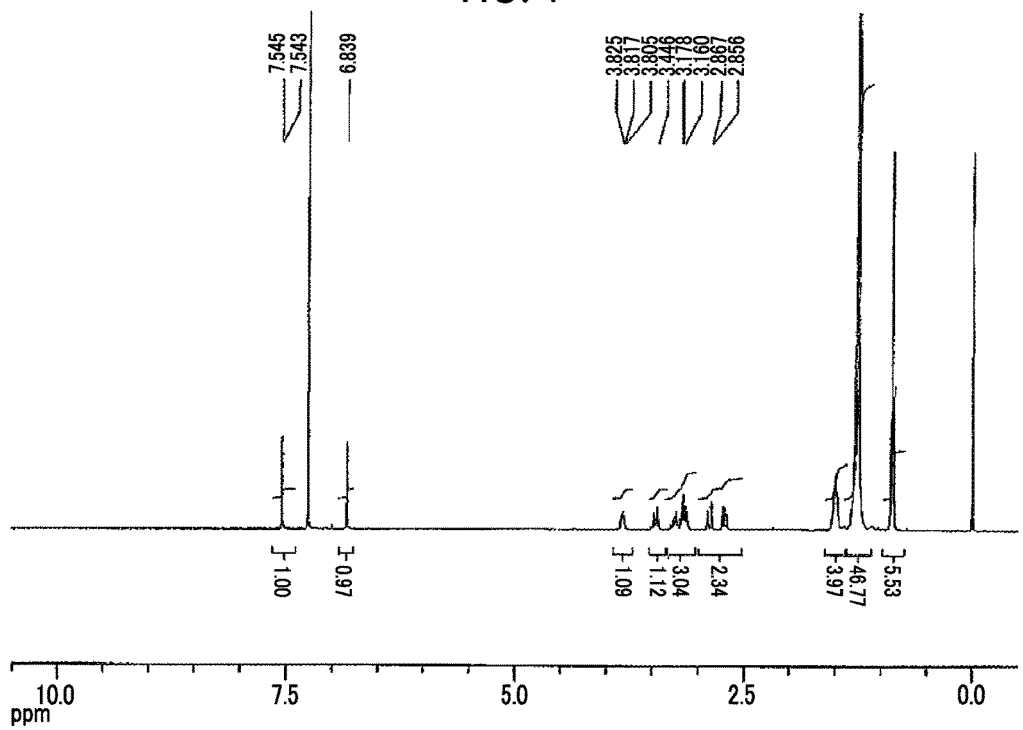
FIG. 1 is a view of $^1$H-NMR of a compound A in Synthesis Example 1.
Figure 2:
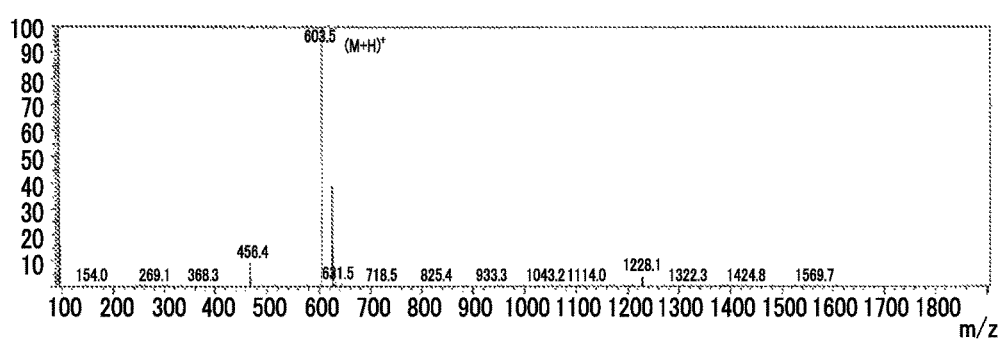
FIG. 2 is a view of an MS spectrum of the compound A in Synthesis Example 1.
Figure 3:
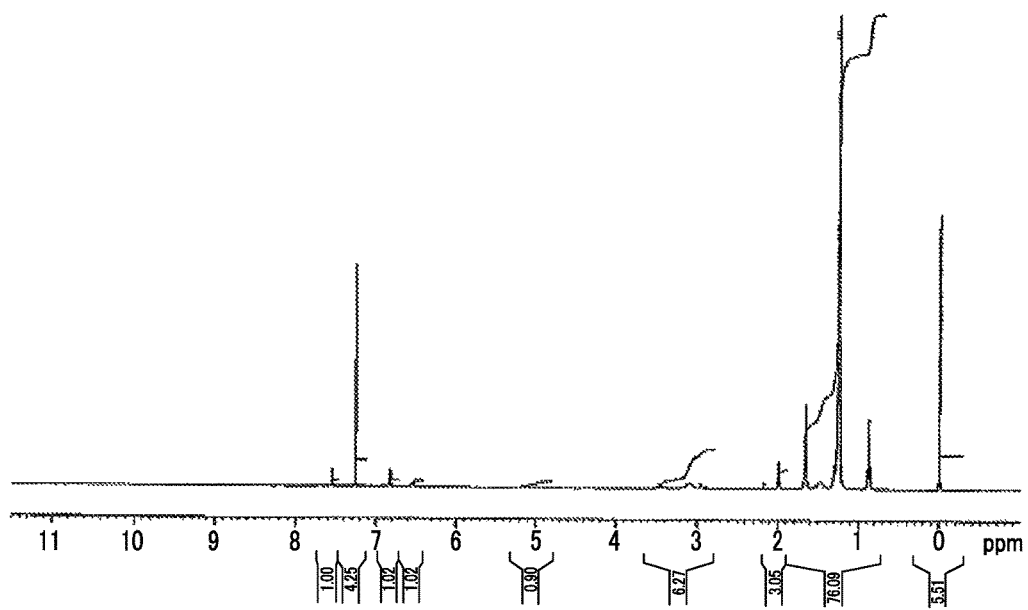
FIG. 3 is a view of $^1$H-NMR of a compound B in Synthesis Example 2.
Figure 4:
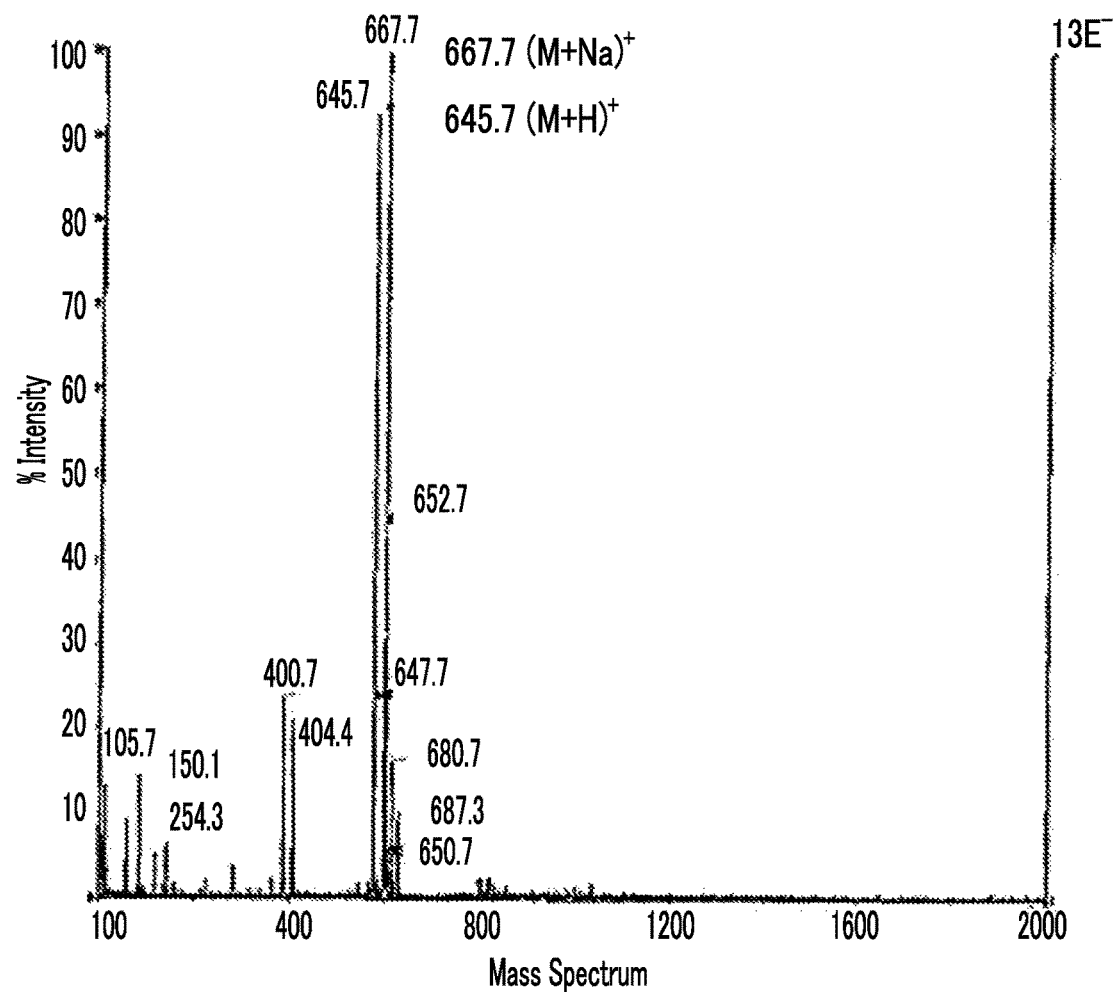
FIG. 4 is a view of an MS spectrum of the compound B in Synthesis Example 2.

Hereinafter, the present invention will be described in detail.

"to" in the present specification indicates a range respectively including numerical values described before and after "to" as minimum values and maximum values.

(1) Component of Lipid Particle

The lipid particles of the present invention are lipid particles containing a compound represented by the following General Formula (1) (where $R^1$ and $R^2$ are the same as or different from each other and are alkyl groups having 10 to 22 carbon atoms), sterol, at least one lipid selected from the group consisting of a neutral lipid and a lipid having a polyethylene glycol (hereinafter, referred to as "PEG") chain, and nucleic acids.

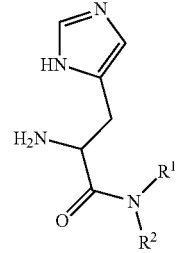

(1)

[Compound Represented by General Formula (1)]

The lipid particles of the present invention contain the compound represented by the following General Formula (1) as a lipid component.

(1)

In the formula, $R^1$ and $R^2$ are the same as or different from each other and mean alkyl groups having 10 to 22 carbon atoms, preferably alkyl groups having 14 to 18 carbon atoms, and more preferably hexadecyl groups.

The compound represented by General Formula (1) has at least one amino group and at least one imidazoyl group. The amino group can strongly hold nucleic acids through an electrostatic interaction. In addition, the imidazoyl group has a positive charge after being protonated at a low pH. Accordingly, fusion between lipid particles and a cell membrane or an endosome membrane easily occurs by introducing the compound represented by General Formula (1) into lipid particles, and therefore, nucleic acids are easily released in a target cell.

The compound represented by General Formula (1) is not particularly limited, and can be synthesized through, for example, the following method.

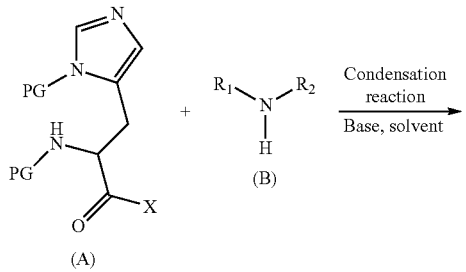

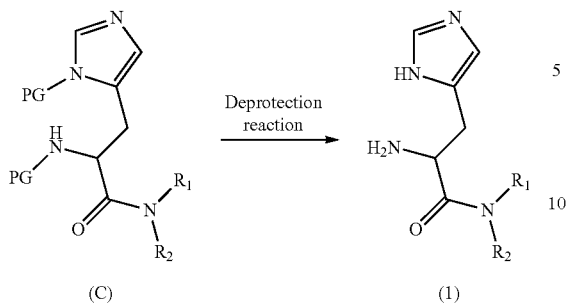

(C) → (1)

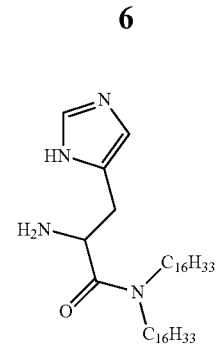

(2)

In the formula, PG represents a protective group and X represents a leaving group constituting an active ester. $R^1$ and $R^2$ are the same as the description above.

That is, after obtaining a compound (C) by reacting an amine derivative (B) with an active ester (A) of histidine protected by a suitable protective group, in the presence of base, it is possible to synthesize the compound represented by General Formula (1) through a suitable deprotection method.

Here, examples of the protective group which can be used in the active ester (A) of histidine include a protective group disclosed in W. Greene et al., Protective Groups in Organic Synthesis 4th edition, pages 255 to 265, 2007, John Wiley & Sons, INC. Specifically, preferred examples thereof include a tert-butoxycarbonyl group (Boc group) and a benzyloxycarbonyl group (Z group).

Examples of the active ester which can be used include a phenyl ester, a trifluorophenyl ester, a pentaphenyl ester, and a hydroxysuccinimide ester. A hydroxysuccinimide ester is preferable from the viewpoint of raw material-obtaining properties or stability.

Examples of the base which can be used include an inorganic base and an organic base. Examples of the inorganic base include sodium hydrogen carbonate or sodium carbonate, and examples of the organic base include triethylamine and diisopropylethylamine. As the base to be used, it is preferable to use a suitable base using a protective group of the active ester (A) of histidine used for a reaction.

The solvent which can be used is not particularly limited, and in general, it is possible to use an organic solvent. Specific examples thereof include an ether-based solvent, an ester-based solvent, an amide-based solvent, and a halogen-based solvent, and preferred examples thereof include ether-based solvents such as tetrahydrofuran and halogen-based solvents such as dichloromethane and chloroform.

Examples of the deprotection reaction which can be used include a method disclosed in W. Greene et al., Protective Groups in Organic Synthesis 4th edition, pages 255 to 265, 2007, John Wiley & Sons, INC.

As the compound represented by General Formula (1) in the present invention, it is more preferable to use the compound (2-amino-N,N-dihexadecyl-3-(1H-imidazol-5-yl)propanamide) [also referred to a compound A in the present specification] represented by Formula (2).

The formulation amount of the compound represented by General Formula (1) in the present invention with respect to the total amount of lipid components of lipid particles is preferably 15 mol % to 60 mol % and more preferably 20 mol % to 50 mol %.

[Sterol]

The lipid particles of the present invention contain sterol. Since sterol has characteristics of deteriorating membrane fluidity, sterol functions as a stabilizer of a membrane in the lipid particles of the present invention.

Sterol used in the present invention is not particularly limited, but examples thereof include cholesterol, phytosterol (sitosterol, stigmasterol, fucosterol, spinasterol, brassicasterol, and the like), ergosterol, cholestanone, cholestenone, coprostenol, cholesteryl-2'-hydroxyethyl ether, and cholesteryl-4'-hydroxybutyl ether.

In the present invention, the formulation amount of sterol with respect to the total amount of constituent components of lipid particles is preferably 10 mol % to 50 mol % and more preferably 15 mol % to 30 mol %.

[At Least One Lipid Selected from Group Consisting of Neutral Lipid and Lipid Having PEG Chain]

The lipid particles of the present invention contain at least one lipid selected from the group consisting of a neutral lipid and a lipid having a PEG chain. In the lipid particles of the present invention, it is possible to obtain an effect of the present invention due to inclusion of at least one of a neutral lipid or a lipid having a PEG chain. It is preferable that the lipid particles of the present invention contain both the neutral lipid and the lipid having a PEG chain. It is possible to further obtain an unexpected stabilization effect with respect to the lipid particles due to the inclusion of both lipids.

(Neutral Lipid)

The neutral lipid used in the present invention is not particularly limited, but examples thereof include phosphatidylcholine, phosphatidylethanolamine, sphingomyelin, and ceramide, and phosphatidylcholine is preferable. In addition, the neutral lipid may be used singly, or a plurality of different neutral lipids may be combined.

The phosphatidylcholine is not particularly limited, but examples thereof include soybean lecithin (SPC), hydrogenated soybean lecithin (HSPC), egg yolk lecithin (EPC), hydrogenated egg yolk lecithin (EPC), dimyristoyl phosphatidylcholine (DMPC), dipalmitoyl phosphatidylcholine (DPPC), distearoyl phosphatidylcholine (DSPC), and 1-palmitoyl-2-oleoyl phosphatidylethanolamine (POPC), and dipalmitoyl phosphatidylcholine (DPPC) is preferable. Among these, dipalmitoyl phosphatidylcholine (DPPC) is preferable as phosphatidylcholine from the viewpoint of phase transition temperature.

The phosphatidylethanolamine is not particularly limited, but examples thereof include dimyristoyl phosphatidylethanolamine (DMPE), dipalmitoyl phosphatidylethanolamine (DPPE), distearoyl phosphatidylethanolamine (DSPE), dioleoyl phosphatidylethanolamine (DOPE), dilinoleoyl phosphatidylethanolamine (DLoPE), diphytanoyl phosphatidylethanolamine (D(Phy)PE), 1-palmitoyl-2-oleoyl phosphatidylethanolamine (POPE), ditetradecyl phosphatidylethanolamine, dihexadecyl phosphatidylethanolamine, dioctadecyl phosphatidylethanolamine, and diphytanyl phosphatidylethanolamine.

The sphingomyelin is not particularly limited, but examples thereof include egg yolk-derived sphingomyelin and milk-derived sphingomyelin.

The ceramide is not particularly limited, but examples thereof include egg-yolk-derived ceramide and milk-derived ceramide.

(Lipid Having PEG Chain)

The lipid having a PEG chain used in the present invention is not particularly limited, but examples thereof include PEG-modified phosphoethanolamine, diacylglycerol PEG derivatives, dialkyl glycerol PEG derivatives, cholesterol PEG derivatives, and ceramide PEG derivatives, and PEG-modified phosphoethanolamine is preferable.

The weight-average molecular weight of a PEG chain is preferably 500 to 5000 and more preferably 750 to 2000.

The PEG chain may be branched or may have a substituent such as a hydroxymethyl group.

In the present invention, the formulation amount of at least one lipid selected from the group consisting of a neutral lipid and a lipid having a PEG chain with respect to the total amount of constituent components of lipid particles is preferably 3 mol % to 55 mol %.

[Nucleic Acid]

Well-known nucleic acids in an arbitrary form are included in the nucleic acids used in the present invention. Specific examples of the nucleic acids include general RNA, DNA, and derivatives thereof. Single-stranded DNA or RNA may be used, double stranded DNA or RNA may be used, and DNA-RNA hybrid may be used. Specific examples of the nucleic acids used in the present invention include antisense DNA, antisense RNA, DNA enzyme, ribozyme, siRNA, shRNA, miRNA, aiRNA, piRNA, decoy nucleic acids, and aptamer. siRNA, miRNA, aiRNA, antisense DNA, and antisense RNA are preferably used as the nucleic acids used in the present invention.

The nucleic acids used in the present invention are not limited to be in a natural type, and may be in a non-natural type, in which at least a part of sugar or phosphate backbone or the like constituting nucleotide is modified in order to improve stability, such as nuclease resistance, in a living body.

Examples of the non-natural nucleic acids in which the sugar portion is modified include 2'-O-methyl RNA, 2'-O-(2-methoxy)ethyl RNA, 2'-deoxy-2'-fluoroarabino nucleic acids, and cross-linked nucleic acids (LNA/BNA). In addition, other examples of the non-natural nucleic acids include peptide nucleic acids (PNA) in which the sugar portion is replaced with peptide, morpholino nucleic acids in which the sugar portion is replaced with morpholino.

Examples of the non-natural nucleic acids in which a phosphate backbone is modified include phosphorothioate body and phosphorodithioate body.

In the present invention, the formulation amount of nucleic acids with respect to the total amount of constituent components of lipid particles is, by molar ratio, preferably 1:10 to 1:5000 and more preferably 1:100 to 1:1000.

(2) Lipid Particle

In the present invention, the lipid particles mean particles constituted of lipids, and are not particularly limited. A liposome having a lamellar structure which is a closed endoplasmic reticulum constituted of a lipid bimolecular membrane is contained in the lipid particles of the present invention. Structures such as a multi liposome (MLV), a small unilamellar liposome (SUV), or a giant unilamellar liposome is known as the liposome, but are not particularly limited thereto. Particles, which do not have the lipid bimolecular membrane structure (lamellar structure) of the above-described liposome, but have a structure in which the inside of a particle is filled with constituent components, are also included in the lipid particles of the present invention.

The form of the lipid formation can be checked through structure analysis through electron microscopic observation or using X-rays. For example, it is possible to confirm that a lipid particle has a lipid bimolecular membrane structure (lamellar structure) like the liposome does and a structure having an internal water layer, or a structure filled with constituent components including lipids since a lipid particle has a core with high electron density in the inside of the particle without having a lipid bimolecular membrane structure (lamellar structure) like the liposome does and an internal water layer, through a method in which Cryo transmission electron microscopy observation (CryoTEM method) is used. It is also possible to check the presence and absence of the lipid bimolecular membrane structure (lamellar structure) in a lipid particle even through X-ray small angle scattering (SAXS) measurement.

The particle diameter of the lipid particles of the present invention is not particularly limited, but is preferably 10 to 1000 nm, more preferably 50 to 500 nm, and still more preferably 75 to 350 nm. The particle diameter of the lipid particles can be measured through a usual method (for example, a dynamic light scattering method or a laser diffraction method).

(3) Production of Lipid Particle

The lipid particles of the present invention are prepared through: step (a) of heating and dissolving an oil phase containing a compound represented by the following General Formula (1) (where $R^1$ and $R^2$ are the same as the above description), sterol, at least one lipid selected from the group consisting of a neutral lipid and a lipid having a PEG chain, an alcohol, and an ester; step (b) of mixing the oil phase obtained in step (a) and a water phase containing nucleic acids; step (c) of cooling the mixed liquid (hereinafter, in some cases, referred to as an oil phase-water phase mixed liquid) which contains the oil phase and the water phase and has been obtained in step (b), and crystallizing lipid particles; and step (d) of removing the alcohol and the ester from the oil phase-water phase mixed liquid obtained in step (c).

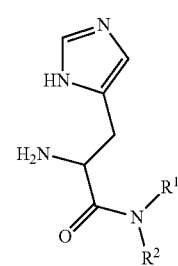

(1)

Sizing or concentration and the like can be performed on the obtained dispersion liquid of lipid particles as necessary. The oil phase means an oily component contained in a composition which is obtained by mixing a compound represented by General Formula (1), sterol, at least one lipid selected from the group consisting of a neutral lipid and a lipid having a PEG chain, an alcohol, and an ester.

In step (a), the temperature in a case of heating the oil phase is preferably 40° C. to 70° C., and more preferably 45° C. to 65° C.

In step (b), the water phase can be obtained by dissolving nucleic acids in water or a buffer solution. Furthermore, a component such as an antioxidant may be added thereto as necessary. The ratio (measure) of mixing the water phase with the oil phase is preferably 3.0:1.0 to 1.0:1.0 and more preferably 1.6:1.0 to 1.1:1.0.

In step (b), the temperature in a case of mixing the water phase with the oil phase is preferably 40° C. to 70° C. and more preferably 45° C. to 65° C. In addition, any mixing time may be selected as long as it is possible to confirm that the entirety of a liquid becomes uniform, and the mixing time is not particularly limited. In addition, any heating time may be selected as long as it is possible to confirm that the temperature of the entirety of a liquid uniformly becomes a desired temperature, and the heating time is not particularly limited.

In step (c) which is a step of cooling the oil phase-water phase mixed liquid and crystallizing lipid particles, the cooling conditions of the oil phase-water phase mixed liquid is preferably 10° C. to 30° C. and more preferably 15° C. to 25° C.

In step (d), the method for removing the alcohol and the ester from the oil phase-water phase mixed liquid in which the lipid particles are crystallized is not particularly limited, and the alcohol and the ester can be removed through a general technique.

Sizing can be performed on lipid particles which have been obtained through this production method as necessary. The sizing method is not particularly limited, and it is possible to reduce the particle diameter using an extruder.

(4) Use of Lipid Particle

It is possible to introduce nucleic acids (genes) into cells by introducing lipid particles of the present invention into the cell in vitro as an example of lipid particles of the present invention.

In a case of using nucleic acids having a medicinal use as nucleic acids contained in the lipid particles of the present invention, the lipid particles of the present invention can be administered into a living body as nucleic acid medicines.

In a case of using the lipid particles of the present invention as nucleic acid medicines, it is possible to administer the lipid particles in the present invention into a living body singly or after being mixed with a dose vehicle (for example, a physiological saline or a phosphate buffer solution) which is pharmaceutically acceptable. The concentration of lipid particles in a mixture mixed with a carrier which is pharmaceutically acceptable is not particularly limited, and can be generally set to 0.05 mass % to 90 mass %. In addition, other additives, for example, a pH adjusting and buffering agent or an osmotic pressure-controlling agent, which are pharmaceutically acceptable, may be added to nucleic acid medicines containing the lipid particles of the present invention.

The administration route when administering nucleic acid medicines containing the lipid particles of the present invention are administered in vivo is not particularly limited, and nucleic acid medicines can be administered through an arbitrary method. Examples of the administration method include oral administration, and parenteral administration (intra-articular administration, intravenous administration, intraperitoneal administration, and muscle administration). Nucleic acid medicines containing the lipid particles of the present invention can also be administered by being directly injected into a disease site.

A dosage form of lipid particles of the present invention is not particularly limited. However, in a case of performing oral administration, the lipid particles of the present invention can be used in forms of tablets, trochiscus, capsules, pills, suspensions, and syrups by being combined with an appropriate diluting agent. In addition, antioxidants, buffering agents, bacteriostats, and additives such as isotonic sterile injections, suspending agents, solubilizing agents, thickening agents, stabilizers, or preservatives can be appropriately included in pharmaceutical preparations suitable for parenteral administration.

(5) Nucleic Acid Delivery Carrier

According to the present invention, it is possible to use lipid particles containing a compound represented by the following General Formula (1) (where $R^1$ and $R^2$ are the same as the above description), sterol, at least one lipid selected from the group consisting of a neutral lipid and a lipid having a PEG chain, and nucleic acids as a nucleic acid delivery carrier (hereinafter, in some cases, referred to as a nucleic acid delivery carrier of the present invention). The nucleic acid delivery carrier of the present invention efficiently releases nucleic acids in a target cell, and therefore, it is possible to obtain significantly favorable drug efficacy. Thus, the nucleic acid delivery carrier of the present invention is significantly useful. That is, according to the present invention, it is possible to provide a nucleic acid delivery carrier containing a compound represented by General Formula (1), sterol, at least one lipid selected from the group consisting of a neutral lipid and a lipid having a PEG chain, and nucleic acids.

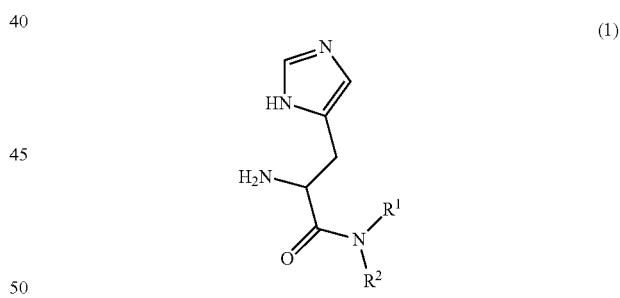

(1)

The nucleic acid delivery carrier of the present invention can introduce nucleic acids into cells by, for example, transfecting the obtained lipid particles into cells in vitro after mixing the lipid particles with the nucleic acids. In addition, the nucleic acid delivery carriers of the present invention are useful as nucleic acid delivery carriers in nucleic acid medicines.

EXAMPLES

The present invention will be described in detail using the following Examples, but the scope of the present invention is not limited to the following Examples.

In addition, in the present invention, CHOLESTEROL HP manufactured by Dishman Pharmaceuticals & Chemicals Ltd. was used as cholesterol, CATSOME-MC6 manufactured by NOF CORPORATION was used as dipalmitoylphosphatidylcholine (DPPC), and SUNBRIGHT DSPE-020CN manufactured by NOF CORPORATION was used as polyethylene glycol-modified phosphoethanolamine (DSPE-PEG, PEG chain molecular weight: 2000).

Synthesis Example 1: Synthesis of Compound (Compound A) Represented by Formula (1)

First Step 23 g of dihexadecylamine and 5.52 g of triethylamine were added to 230 mL of tetrahydrofuran, 24.6 g of Boc-His(1-Boc)-OSU was added thereto while stirring the mixture, which was then stirred for one hour at room temperature and was stirred for five hours at 50° C. Thereafter, tetrahydrofuran was distilled off under reduced pressure and 450 mL of chloroform and 200 mL of water were added to the reactant. An organic layer was separately taken, sequentially washed with a saturated sodium hydrogen carbonate aqueous solution, a 10% citric acid aqueous solution, and a saturated sodium chloride aqueous solution, and dried with anhydrous magnesium sulfate to distil off a solvent under reduced pressure. The residue was purified through silica gel column chromatography (hexane/ethyl acetate=5/1 to 3/1) and 24 g of a protected substance of an oily matter was obtained.

Boc-His (1-Boc)-OSU

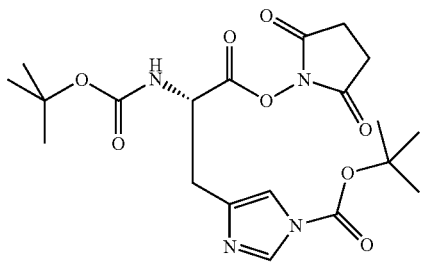 [SMILES: CC(C)(C)OC(=O)N[C@@H](Cc1cn(C(=O)OC(C)(C)C)cn1)C(=O)ON1C(=O)CCC1=O]

Second Step 21.7 g of the protected substance which had been obtained in the first step was added to 35 mL of trifluoroacetic acid little by little, and the mixture was stirred for 24 hours at room temperature. Thereafter, the mixture was gradually added to 600 mL of an aqueous solution containing 40 g of saturated sodium bicarbonate and was stirred for one hour. 500 mL of chloroform was added to the obtained reaction liquid, an organic layer was separately taken, sequentially washed with a saturated sodium hydrogen carbonate aqueous solution and a saturated sodium chloride aqueous solution, and dried with anhydrous magnesium sulfate to distil off a solvent under reduced pressure. The residue was purified through silica gel chromatography (chloroform/methanol=10/1) and 11.6 g of a compound A of a colorless solid was obtained. Identification of the compound was performed through NMR and MS.

Synthesis Example 2: Synthesis of Compound for Comparison (Compound B)

3.00 g of N-acetyl-histidine, 225 mL of dimethylacetamide, and 4.2 mL of triethylamine were taken into a reaction container and were stirred at an internal temperature of 25° C. 2.92 g of 1-ethyl-3-(3-dimethylaminopropyl)carbodiimide hydrochloride was further added thereto and the mixture was stirred at an internal temperature of 45° C. to make a homogenous solution. 7.09 g of dihexadecylamine was added thereto and the mixture was stirred for eight hours at an internal temperature of 45° C. After cooling the reaction mixture, an organic layer was extracted using an ethyl acetate, dried with anhydrous magnesium sulfate to distil off a solvent under reduced pressure. The residue was purified through silica gel column chromatography and 1.11 g of a compound B represented by the following Formula was obtained.

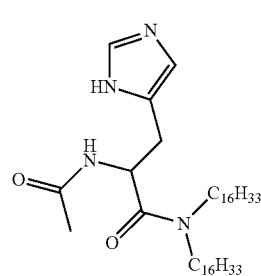

Example 1

(Coacervation Method)
Preparation of Oil Phase 37 mg, 30 mg, 33 mg, and 20 mg of respective L-α-dipalmitoylphosphatidylcholine, a compound A, cholesterol, N-(carbonyl-methoxypolyethylene glycol 2000)-1,2-distearoyl-sn-glycero-3-phosphoethanolamine sodium salts (hereinafter, DSPE-PEG) were measured so as to make a molar ratio of 26/26/44/4, and 0.3 mL of ethanol and 0.7 mL of an ethyl acetate were added thereto and were dissolved to obtain an oil phase.

Preparation of Nucleic Acid-Holding Lipid Particle 0.25 mL of an aqueous solution of nucleic acids, which had been obtained by dissolving 5 mg of siRNA to be described below in 0.263 mL of sterilized water, was added to the oil phase obtained in the above-described step and 1.0 mL of sterilized water was further added thereto. The mixture was heated for 10 minutes at 55° C. Thereafter, the mixture was allowed to cool at room temperature while being stirred. Subsequently, dialysis was performed at room temperature using a 100 mM histidine solution to remove an ethanol/ethyl acetate-mixed solution. The obtained solution was graded by being passed through a 0.4 μm filter using an extruder (Mini Extruder manufactured by Avanti Lipids Polar, Inc.) to obtain lipid particles holding nucleic acids (hereinafter, in some cases, referred to as nucleic acid-holding lipid particles).

Examples 2 to 4 and 6/Comparative Examples 1 and 2

Examples 2 to 4 and 6 and Comparative Examples 1 and 2 are prepared through the same method as that in Example 1 in accordance with prescriptions respectively shown in Table 1 to obtain target lipid particle dispersion liquids.

Evaluation of Target mRNA Survival Rate in Cell

Evaluation of a mRNA survival rate was performed on Examples 1 to 4 and 6 and Comparative Examples 1 and 2 through the following technique.

(1) Transfection of Lipid Particle into Cell

Regarding 24-hole plate seeded with 0.9×10³ TOV112D cells (human ovarian cancer cell strain), a medium was exchanged with 200 μL of Opti-MEM (registered trademark) on the following day. Next, 100 μL of each of the liposome dispersion liquids which had been prepared in Examples 1 to 4 and 6 and Comparative Examples 1 and 2 and had been diluted with Opti-MEM (registered trademark) so as to become a concentration of 300 nM was added to the 24-hole plate. The final concentration was adjusted to 100 nM (total liquid amount of 300 μl). Thereafter, culturing was performed for 24 hours to 48 hours in a 5% $CO_2$ incubator.

(2) Total RNA Extraction

After the culturing, total RNA was extracted from the cells using RNeasy Mini Kit (QIAGEN, registered trademark). After measuring absorbency of the total RNA concentration after the extraction, dilution was performed using RNase-free water such that the concentration of RNA became 5 ng/μL.

(3) Quantitative PCR Reaction

A reverse transcription reaction and a PCR reaction were performed using QUANTIFAST PROBE RT-PCR KIT (QIAGEN, registered trademark). TaqMan Gene expression assay (ABI, registered trademark) was used as a primer and a probe with respect to siRNA genes which had been used. Quantitative PCR was performed using MX3000P (Agilent Technologies, registered trademark). The conditions of PCR were set to 50° C. for 30 minutes, 95° C. for 15 minutes, 94° C. for 15 seconds, and 60° C. for 30 seconds (40 cycles). TaqMan Endogeneous Control Human ACTB (ABI, registered trademark) was used as an internal standard. The obtained data was calculated as an mRNA survival rate through relative quantitative determination with respect to no processing of transfection using a ΔΔCT method.

Example 5

In Example 5, transfection of cells into lipid particles was performed in the same manner as in Example 1 except that the transfection was performed by exchanging opti-MEN with opti-MEN in which 10% blood serum was included.

siRNAs having the following sequences were used.

```
(sense chain)
                                      (SEQ ID No: 1)
5'-GUUCAGACCACUUCAGCUU-3'

(antisense chain)
                                      (SEQ ID No: 2)
3'-CAAGUCUGGUGAAGUCGAA-5'
```

Each mRNA production inhibition rate in a case where Examples 1 to 6 and Comparative Examples 1 and 2 were used was shown in Table 1.

TABLE 1

| | | Example 1 | Example 2 | Example 3 | Example 4 | Example 5 | Example 6 | Comparative Example 1 | Comparative Example 2 |
|---|---|---|---|---|---|---|---|---|---|
| Lipids components | Compound A (mol %) | 26.0 | 26.0 | 26.0 | 26.0 | 26.0 | 15.0 | 26.0 | — |
| | Compound B (mol %) | — | — | — | — | — | — | — | 26.0 |
| | Cholesterol (mol %) | 44.0 | 30.0 | 20.0 | 10.0 | 44.0 | 20.0 | 0.0 | 26.0 |
| | DPPC (mol %) | 26.0 | 36.0 | 46.0 | 60.0 | 26.0 | 57.0 | 70.0 | 44.0 |
| | DSPE-PEG (mol %) | 4.0 | 8.0 | 8.0 | 4.0 | 4.0 | 8.0 | 4.0 | 4.0 |
| Serum | | None | None | None | None | Present | None | None | None |
| mRNA survival rate (%) | | 6.0 | 4.0 | 8.0 | 14.0 | 6.0 | 8.0 | 100 | 101 |

As shown in Table 1, it was found that the liposome dispersion liquids shown in Examples 1 to 6 exhibit a significantly high effect of inhibiting production of mRNA, and it is possible to stably hold nucleic acid molecules outside cells (in blood), and to efficiently exhibit an original function of nucleic acids in a target cell due to prompt release of nucleic acids in cytoplasm.

What is claimed is:

1. Lipid particles comprising:
a compound represented by the following General Formula (1);
sterol;
a neutral lipid;
a lipid having a polyethylene glycol chain; and
nucleic acids,

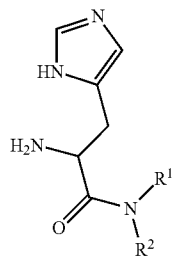

(1)

in the formula, $R^1$ and $R^2$ are the same as or different from each other, and are alkyl groups having 10 to 22 carbon atoms;
wherein the neutral lipid is dipalmitoyl phosphatidylcholine;
the content of the compound represented by General Formula (1) is 15 mol % to 60 mol % of total lipid present in the particle without nucleic acids;
the content of sterol is 10 mol % to 50 mol % of total lipid present in the particle without nucleic acids; and
the content of dipalmitoyl phosphatidylcholine is 26 mol % to 60 mol % of total lipid present in the particle without nucleic acids.

2. The lipid particles according to claim 1,
wherein the content of a neutral lipid and a lipid having polyethylene glycol chain is 30 mol % to 55 mol % of total lipid present in the particle without nucleic acids.

3. The lipid particles according to claim 1,
wherein the sterol is cholesterol.

4. The lipid particles according to claim 2,
wherein the sterol is cholesterol.

5. The lipid particles according to claim 1,
wherein the lipid having a polyethylene glycol chain is phosphoethanolamine which has been modified with polyethylene glycol.

6. The lipid particles according to claim 2,
wherein the lipid having a polyethylene glycol chain is phosphoethanolamine which has been modified with polyethylene glycol.

7. A nucleic acid delivery carrier comprising:
a compound represented by the following General Formula (1);
sterol;
a neutral lipid;
a lipid having a polyethylene glycol chain; and
nucleic acids,

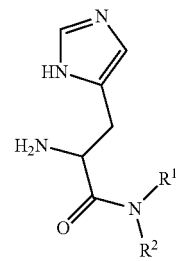

(1)

in the formula, $R^1$ and $R^2$ are the same as or different from each other and are alkyl groups having 10 to 22 carbon atoms;
wherein the neutral lipid is dipalmitoyl phosphatidylcholine;
the content of the compound represented by General Formula (1) is 15 mol % to 60 mol % of total lipid present in the particle without nucleic acids;
the content of sterol is 10 mol % to 50 mol % of total lipid present in the particle without nucleic acids; and
the content of dipalmitoyl phosphatidylcholine is 26 mol % to 60 mol % of total lipid present in the particle without nucleic acids.

8. The lipid particles according to claim 7,
wherein the sterol is cholesterol.

* * * * *